United States Patent
Kyle et al.

(10) Patent No.: US 11,584,196 B2
(45) Date of Patent: Feb. 21, 2023

(54) ULTRA-VIOLET LIGHT SANITIZING OF A VEHICLE

(71) Applicant: Toyota Motor North America, Inc., Plano, TX (US)

(72) Inventors: Roger Akira Kyle, Frisco, TX (US); Timothy Wang, Ypsilanti, MI (US); Bryan E. Yamasaki, Ypsilanti, MI (US)

(73) Assignee: Toyota Motor North America, Inc., Plano, TX (US)

( * ) Notice: Subject to any disclaimer, the term of this patent is extended or adjusted under 35 U.S.C. 154(b) by 182 days.

(21) Appl. No.: 16/904,813

(22) Filed: Jun. 18, 2020

(65) Prior Publication Data

US 2021/0394590 A1 Dec. 23, 2021

(51) Int. Cl.
*A61L 2/10* (2006.01)
*A61L 2/24* (2006.01)
*B60H 3/00* (2006.01)
*A61L 9/20* (2006.01)

(52) U.S. Cl.
CPC .............. *B60H 3/0014* (2013.01); *A61L 2/10* (2013.01); *A61L 2/24* (2013.01); *A61L 9/20* (2013.01); *B60H 3/0035* (2013.01); *A61L 2202/11* (2013.01); *A61L 2202/14* (2013.01); *A61L 2202/16* (2013.01); *A61L 2202/25* (2013.01); *A61L 2209/111* (2013.01)

(58) Field of Classification Search
CPC .......... A61L 2/10; A61L 2/24; B60H 3/0014; B60H 3/0035
See application file for complete search history.

(56) References Cited

U.S. PATENT DOCUMENTS

| | | |
|---|---|---|
| 6,366,220 B1 | 4/2002 | Elliott |
| 9,124,955 B2 | 9/2015 | Geva et al. |
| 9,676,250 B2 | 6/2017 | Weast et al. |
| 10,219,750 B2 | 3/2019 | Duan et al. |
| 10,354,460 B2 | 7/2019 | Ricci |
| 2019/0091738 A1 | 3/2019 | Chen |
| 2020/0061223 A1* | 2/2020 | Hallack .................. B60N 2/002 |

FOREIGN PATENT DOCUMENTS

| | | |
|---|---|---|
| JP | 2003148967 A | 5/2003 |
| JP | 2006302206 A | 11/2006 |

* cited by examiner

*Primary Examiner* — Kevin Joyner
(74) *Attorney, Agent, or Firm* — Christopher G. Darrow; Darrow Mustafa PC

(57) ABSTRACT

A system that can selectively activate or deactivate one or more ultra-violet light sources to sanitize a portion of a vehicle. The system can include a vehicle that has a vehicle door. The system can include one or more sensors that can be configured to detect whether the vehicle door is open or closed. In response to detecting that the vehicle door is open, the system can cause the one or more ultra-violet light sources to be activated, whereby ultra-violet light is emitted by the one or more ultra-violet light sources with respect to at least a portion of the vehicle. In some instances, the ultra-violet light can be emitted across the door frame of an open door. In some instances, the ultra-violet light can be emitted within at least a portion of the vehicle cabin.

10 Claims, 3 Drawing Sheets

ULTRA-VIOLET LIGHT SANITIZING OF A VEHICLE

FIELD

The subject matter described herein relates in general to vehicles and, more particularly, to sanitizing a vehicle.

BACKGROUND

Ultra-violet light (such as UV-B and UV-C) may be used as a germicidal agent. Disinfection may be achieved by killing or inactivating various microorganisms.

SUMMARY

In one respect, the subject matter presented herein is directed to a system that can sanitize at least a portion of a vehicle and/or minimize or prevent contamination of a vehicle cabin. The system can include a vehicle that has a vehicle door. The system can include one or more sensors, which can be configured to detect whether the vehicle door is open or closed. The system can include one or more ultra-violet light sources. The system can include one or more processors that can be operatively connected to selectively activate or deactivate the one or more ultra-violet light sources. The one or more processors can be programmed to initiate executable operations. The executable operations can include, responsive to detecting that the vehicle door is open, causing the one or more ultra-violet light sources to be activated, whereby ultra-violet light is emitted by the one or more ultra-violet light sources with respect to at least a portion of the vehicle.

DETAILED DESCRIPTION

Figure 1:
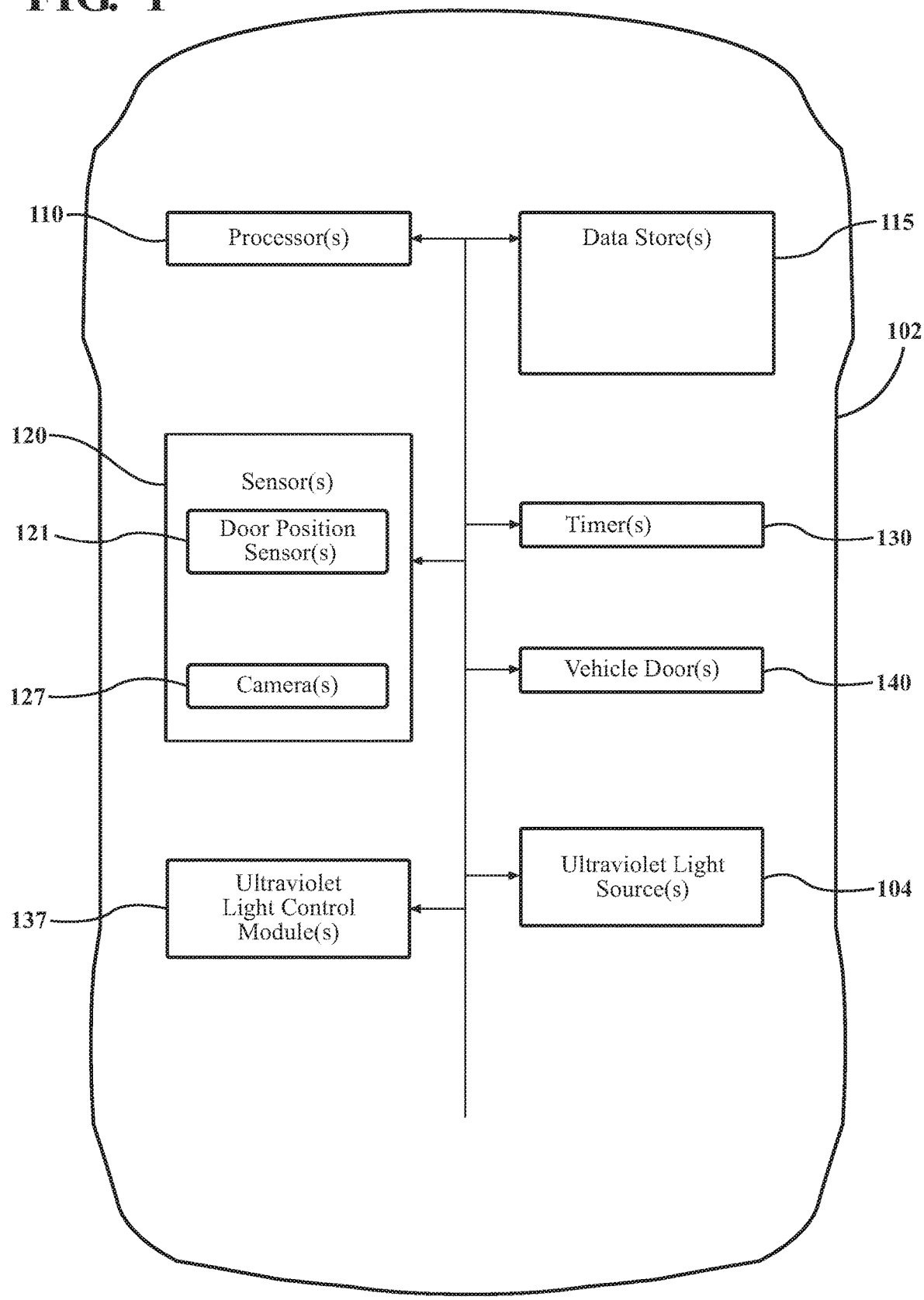
FIG. 1 is an example of a vehicle.

Vehicle cabins can harbor germs and various microorganisms harmful to humans. The germs and microorganisms can be introduced into the vehicle cabin in various ways, such as by people repeatedly entering and exiting the vehicle, bringing different items into the vehicle, and/or outside air infiltrating the vehicle cabin when a door is open. According to arrangements herein, a system can be configured to sanitize at least a portion of a vehicle using ultra-violet light. Additionally, the system can minimize or prevent germs and microorganisms in the external environment of a vehicle from entering the vehicle cabin. The system can be configured such that, in response to detecting that a vehicle door is open, one or more ultra-violet light sources can be activated. For instance, the ultra-violet light sources can be operatively positioned to emit ultra-violet light across the vehicle door frame and/or within the vehicle cabin. The system can deactivate the ultra-violet light sources in response detecting that the vehicle door is closed and/or that a predetermined time period has expired.

Detailed embodiments are disclosed herein; however, it is to be understood that the disclosed embodiments are intended only as examples. Therefore, specific structural and functional details disclosed herein are not to be interpreted as limiting, but merely as a basis for the claims and as a representative basis for teaching one skilled in the art to variously employ the aspects herein in virtually any appropriately detailed structure. Further, the terms and phrases used herein are not intended to be limiting but rather to provide an understandable description of possible implementations. Various embodiments are shown in FIGS. 1-4, but the embodiments are not limited to the illustrated structure or application.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details.

Referring to FIG. 1, an example of a vehicle 102 is shown. As used herein, "vehicle" means any form of motorized transport. In one or more implementations, the vehicle 102 can be an automobile. While arrangements will be described herein with respect to automobiles, it will be understood that embodiments are not limited to automobiles. In some implementations, the vehicle 102 may be a watercraft, an aircraft, or any other form of motorized transport.

The vehicle 102 can have a manual operational mode in which all of or a majority of the navigation and/or maneuvering of the vehicle 102 is performed by a human driver. In one or more arrangements, the vehicle 102 can be a conventional vehicle that is configured to operate in only a manual mode.

In one or more arrangements, the vehicle 102 can be an autonomous vehicle. As used herein, "autonomous vehicle" means a vehicle that configured to operate in an autonomous operational mode. "Autonomous operational mode" means that one or more computing systems are used to navigate and/or maneuver the vehicle along a travel route with minimal or no input from a human driver. In one or more arrangements, the vehicle 102 can be highly automated or completely automated.

The vehicle 102 can have one or more semi-autonomous operational modes in which a portion of the navigation and/or maneuvering of the vehicle along a travel route is performed by one or more computing systems, and a portion of the navigation and/or maneuvering of the vehicle along a travel route is performed by a human driver. Examples of a semi-autonomous operational mode is when an adaptive cruise control and/or lane keeping is activated.

The vehicle 102 can be configured to be switched between the various operational modes, including between any of the above-described operational modes.

The vehicle 102 can include various elements. Some of the possible elements of the vehicle 102 are shown in FIG. 1 and will now be described. It will be understood that it is not necessary for the vehicle 102 to have all of the elements shown in FIG. 1 or described herein. The vehicle 102 can have any combination of the various elements shown in FIG. 1. Further, the vehicle 102 can have additional elements to those shown in FIG. 1. In some arrangements, the vehicle 102 may not include one or more of the elements shown in FIG. 1. Further, while the various elements are shown as being located within the vehicle 102 in FIG. 1, it will be understood that one or more of these elements can be located external to the vehicle 102. Further, the elements shown may be physically separated by large distances.

The vehicle 102 can include one or more processors 110. "Processor" means any component or group of components that are configured to execute any of the processes described herein or any form of instructions to carry out such processes or cause such processes to be performed. The processor(s) 110 may be implemented with one or more general-purpose and/or one or more special-purpose processors. Examples of suitable processors include microprocessors, microcontrollers, DSP processors, and other circuitry that can execute software. Further examples of suitable processors include, but are not limited to, a central processing unit (CPU), an array processor, a vector processor, a digital signal processor (DSP), a field-programmable gate array (FPGA), a programmable logic array (PLA), an application specific integrated circuit (ASIC), programmable logic circuitry, and a controller. The processor(s) 110 can include at least one hardware circuit (e.g., an integrated circuit) configured to carry out instructions contained in program code. In arrangements in which there is a plurality of processors 110, such processors can work independently from each other or one or more processors can work in combination with each other. In one or more arrangements, the processor(s) 110 can be a main processor of the vehicle 102. For instance, the processor(s) 110 can be an electronic control unit (ECU).

The vehicle 102 can include one or more data stores 115 for storing one or more types of data. The data store 115 can include volatile and/or non-volatile memory. Examples of suitable data stores 115 include RAM (Random Access Memory), flash memory, ROM (Read Only Memory), PROM (Programmable Read-Only Memory), EPROM (Erasable Programmable Read-Only Memory), EEPROM (Electrically Erasable Programmable Read-Only Memory), registers, magnetic disks, optical disks, hard drives, or any other suitable storage medium, or any combination thereof. The data store 115 can be a component of the processor(s) 110, or the data store 115 can be operatively connected to the processor(s) 110 for use thereby. The term "operatively connected," as used throughout this description, can include direct or indirect connections, including connections without direct physical contact.

The vehicle 102 can include one or more vehicle doors 140. The vehicle 102 can include one or more vehicle door frames that can receive the one or more vehicle doors 140. The vehicle doors 140 can be on any suitable side (e.g., a front side, a lengthwise side, a rear side) of the vehicle 102. As an example, the vehicle door 140 can be a driver's door, a passenger's door, and/or a rear door (or trunk door).

The vehicle 102 can include a vehicle cabin. The vehicle cabin can include a compartment or seating area for passengers. The vehicle cabin can be separated from an external environment of the vehicle by a body of the vehicle 102. The cabin can be defined by one or more components, which can include the vehicle door(s) 140.

The vehicle 102 can include one or more sensors 120. "Sensor" means any device, component and/or system that can detect, determine, assess, monitor, measure, quantify and/or sense something. The one or more sensors 120 can detect, determine, assess, monitor, measure, quantify and/or sense in real-time. As used herein, the term "real-time" means a level of processing responsiveness that a user or system senses as sufficiently immediate for a particular process or determination to be made, or that enables the processor to keep up with some external process. Data acquired by the one or more sensors 120 can be stored in the data store(s) 115.

In arrangements in which there is a plurality of sensors, the sensors can work independently from each other. Alternatively, two or more of the sensors can work in combination with each other. In such case, the two or more sensors can form a sensor network. The one or more sensors can be operatively connected to the processor(s) 110, the data store(s) 115, and/or other element of the vehicle 102 (including any of the elements shown in FIG. 1).

The sensor(s) 120 can be any suitable type of sensor. Various examples of different types of sensors will be described herein. However, it will be understood that the embodiments are not limited to the particular sensors described.

The sensor(s) 120 can include one or more door position sensors 121. The door position sensor 121 can be configured to detect or acquire information about whether the vehicle door(s) 140 is open or closed. Additionally, the door position sensor(s) 121 can be configured to determine how long the vehicle door has been opened, how long the vehicle door has been closed, and/or which vehicle door is opened or closed. The door position sensor(s) 121 can be any suitable sensor, now known or later developed. For instance, the door position sensor(s) 121 can be proximity sensors, motion sensors, cameras, or contact sensors, just to name a few possibilities. As an example, the camera(s) 127 may acquire one or more still images and/or videos of a portion of the vehicle door(s) 140. As another example, in a case where the vehicle door 140 is connected by a hinge to the vehicle door frame receiving the vehicle door, the door position sensor 121 may include one or more touch-sensitive buttons located along the hinge. The one or more touch-sensitive buttons may be spaced along the hinge such that as the vehicle door 140 opens or closes, a different touch-sensitive button is making contact with an edge of the vehicle door frame, generally indicating an angle at which the vehicle door 140 is open. As another example, a timer 130 can start when the vehicle door 140 is open and is reset when the vehicle door 140 is closed. The timer 130 can be a part of the door position sensor(s) 121, or the timer 130 can be a separate element.

The vehicle 102 can include one or more ultra-violet light sources 104. The processor(s) 110 can be operatively connected to selectively activate or deactivate the ultra-violet light source(s) 104. The ultra-violet light source(s) 104 can be any suitable source that emits ultra-violet light, now known or later developed. For instance, the ultra-violet light source(s) 104 can be an LED (light emitting diode). The UV light can be configured to kill or inactivate bacteria, viruses, infectious agents, and/or microorganism(s) while also being safe for human/animal exposure. The ultra-violet light source(s) 104 can emit any suitable ultra-violet light such as a UV-C light between 200 and 280 nm. As an example, the ultra-violet light source(s) 104 can emit short-wavelength ultra-violet (ultra-violet C or UVC) light to kill or inactivate microorganism(s) in the air. As an example, the ultra-violet light source(s) 104 can emit Far-UVC light. The ultra-violet light source(s) 104 can be operatively connected to receive power from any suitable power source (e.g., a battery).

The ultra-violet light source(s) 104 can be operatively positioned to emit ultra-violet light with respect to certain portions of the vehicle 102. For example, the ultra-violet light source(s) 104 can be configured to emit ultra-violet light across the vehicle door frame. As an example the ultra-violet light source(s) 104 can generate an ultra-violet light curtain that at least partially separates the vehicle cabin and an external environment of the vehicle 102. Thus, the ultra-violet light source(s) 104 can be operatively positioned with respect to the vehicle door frame. In such a case, the ultra-violet light source(s) 104 can be a plurality of ultra-violet lights operatively connected to a first portion of the vehicle door frame. The ultra-violet lights can emit ultra-violet light toward an opposite portion of the vehicle door frame. The ultra-violet lights can be spaced, positioned, and/or oriented such that the ultra-violet light emitted by the ultra-violet lights can cover the area across at least a portion of the vehicle door frame.

The ultra-violet light source(s) 104 can be operatively positioned to emit ultra-violet light downwardly. In such a case and as an example, the ultra-violet light source(s) 104 can be a plurality of ultra-violet lights operatively connected to a top portion of the vehicle door frame with the ultra-violet lights emitting ultra-violet light toward a bottom portion of the vehicle door frame. As another example, the ultra-violet light source(s) 104 can be operatively connected to one or more portions of the vehicle door frame such as the top portion, bottom portion, and/or side portions of the vehicle door frame.

The ultra-violet light source(s) 104 can be operatively positioned to emit ultra-violet light in at least a portion of the vehicle cabin. In such a case, the ultra-violet light source(s) 104 can be operatively connected to a ceiling portion inside the vehicle cabin.

The vehicle 102 can include one or more modules, which will be described herein. The modules can be implemented as computer readable program code that, when executed by a processor, implement one or more of the various processes described herein. One or more of the modules can be a component of the processor(s) 110, or one or more of the modules can be executed on and/or distributed among other processing systems to which the processor(s) 110 is operatively connected. The modules can include instructions (e.g., program logic) executable by one or more processor(s) 110. Alternatively or in addition, one or more data store 115 may contain such instructions.

In one or more arrangements, one or more of the modules described herein can include artificial or computational intelligence elements, e.g., neural network, fuzzy logic or other machine learning algorithms. Further, in one or more arrangements, one or more of the modules can be distributed among a plurality of the modules described herein. In one or more arrangements, two or more of the modules described herein can be combined into a single module.

The vehicle 102 can include one or more ultra-violet light control modules 137. The ultra-violet light control module(s) 137 can be configured to selectively activate or deactivate the ultra-violet light source(s) 104.

The ultra-violet light control module(s) 137 can analyze data acquired by the door position sensor(s) 121 to determine whether a vehicle door is opened or closed. Alternatively, the ultra-violet light control module(s) 137 can receive an indication from the door position sensor(s) 121 that a vehicle door is opened or closed. The ultra-violet light control module(s) 137 can, responsive to detecting that the vehicle door 140 is open, cause the ultra-violet light source(s) 104 to be activated. The activated ultra-violet light source(s) 104 can emit ultra-violet light with respect to at least a portion of the vehicle 102. As an example and as previously mentioned, the activated ultra-violet light source(s) 104 can emit ultra-violet light as a curtain across the vehicle door frame. As another example, additionally and/or alternatively, the activated ultra-violet light source(s) 104 can emit ultra-violet light toward the inside of the vehicle cabin.

The ultra-violet light control module(s) 137 can, responsive to detecting that the vehicle door 140 is closed, cause the ultra-violet light source(s) 104 to be deactivated or remain deactivated. In such a case, ultra-violet light is not emitted by the ultra-violet light source(s) 104. Additionally and/or alternatively, the ultra-violet light control module(s) 137 can, responsive to the vehicle door 140 being open for a predetermined time period (as indicated by the timer 130), cause the one or more ultra-violet light source(s) 104 to be deactivated. The ultra-violet light control module(s) 137 can determine the predetermined time period based on a suitable time period for the ultra-violet light emission to be effective. The predetermined time period can be configured by a user or some other entity (e.g., a vehicle manufacturer). As an example, when the vehicle door 140 is opened, the timer 130 can start. If the vehicle door 140 is still open when the timer 130 reaches ninety (90) seconds or other predetermined time period, the ultra-violet light control module(s) 137 can cause the ultra-violet light source(s) 104 to be deactivated and stop emitting ultra-violet light.

Now that the various potential systems, devices, elements and/or components of the vehicle 102 have been described, an example method will now be described. Various possible steps of such method will now be described. The method described may be applicable to the arrangements described above, but it is understood that the methods can be carried out with other suitable systems and arrangements. Moreover, the method may include other steps that are not shown here, and in fact, the method are not limited to including every step shown. The blocks that are illustrated here as part of the method are not limited to the particular chronological order. Indeed, some of the blocks may be performed in a different order than what is shown and/or at least some of the blocks shown can occur simultaneously.

Figure 2:
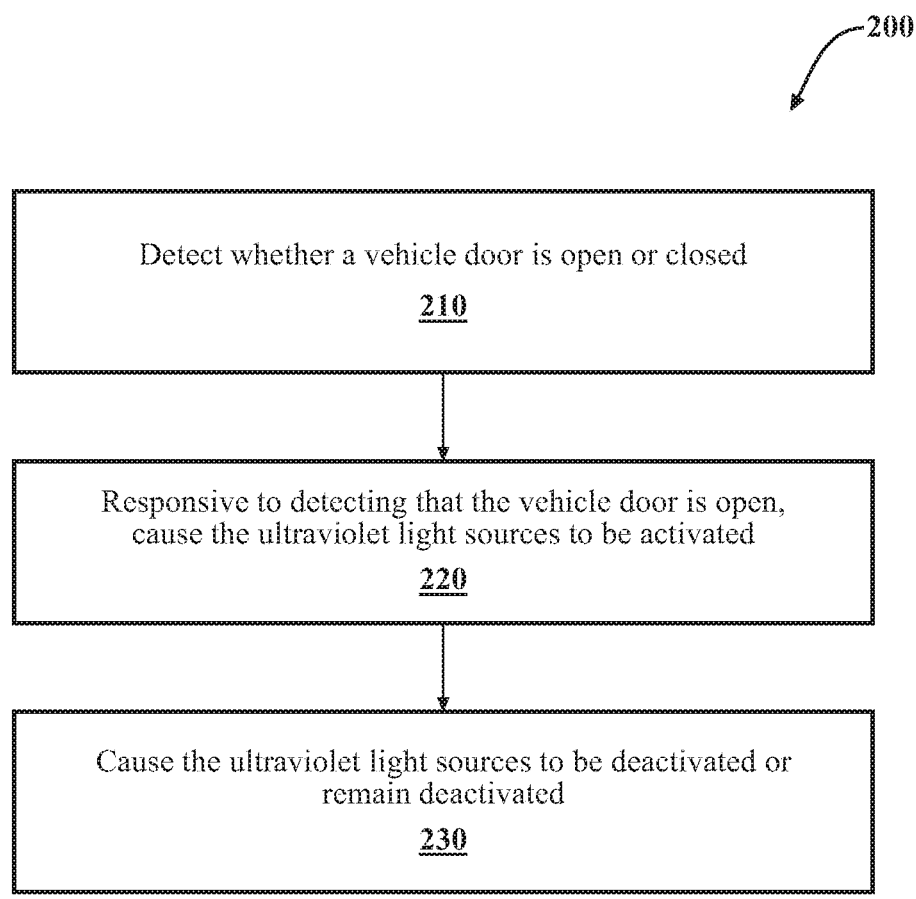
FIG. 2 is an example of a vehicle sanitization method.

Referring now to FIG. 2, an example of a vehicle sanitization method is shown. At block 210, it can be detected whether the vehicle door 140 is open or closed. As mentioned above and as an example, the door position sensor(s) 121 can detect whether the vehicle door 140 is open or closed. The method 200 can continue to block 220.

At block 220, the ultra-violet light source(s) 104 can be caused to be activated in response to detecting that the vehicle door 140 is open. More specifically, the ultra-violet light control module(s) 137 can, responsive to detecting that the vehicle door 140 is open, cause the ultra-violet light source(s) 104 to be activated. As previously mentioned, the ultra-violet light can be emitted by the activated ultra-violet light source(s) 104 with respect to at least a portion of the vehicle 102. In some implementations, the ultra-violet light source(s) 104 can emit ultra-violet light across the vehicle door frame. In such a case, the ultra-violet light source(s) 104 can effectively generate an ultra-violet light curtain that can at least partially separate the vehicle cabin and an external environment of the vehicle 102. Thus, the ultra-violet light curtain can at least partially separate the air in the vehicle cabin from the air in the external environment of the vehicle 102.

Alternatively or additionally, the ultra-violet light source(s) 104 can emit ultra-violet light in at least a portion of the vehicle cabin. In such a case, the ultra-violet light source(s) 104 can be operatively connected to a portion of the vehicle cabin such as the ceiling of the vehicle cabin, and the ultra-violet light source(s) can emit ultra-violet light into the vehicle cabin in response to the sensor(s) 120 detecting that the vehicle door 140 is open. The method 200 can continue to block 230.

At block 230, the ultra-violet light source(s) 104 can be deactivated or remain deactivated. More specifically, the ultra-violet light control module(s) 137 can deactivate the ultra-violet light source(s) 104 such that ultra-violet light is not emitted by the ultra-violet light source(s) 104. In some arrangements, the ultra-violet light control module(s) 137 can deactivate the ultra-violet light source(s) 104 in response to the sensor(s) 120 detecting that the vehicle door 140 is closed. Alternatively or additionally, the ultra-violet light control module(s) 137 can deactivate the ultra-violet light source(s) 104 in response to the vehicle door(s) 140 being open for a predetermined time period. In such a case, when a timer 130 that started upon detecting that the vehicle door 140 is open reaches the predetermined time period, the ultra-violet light control module(s) 137 can deactivate the ultra-violet light source(s) 104. The method 200 can end. Alternatively, the method 200 can return to block 210 or some other block.

Figure 3:
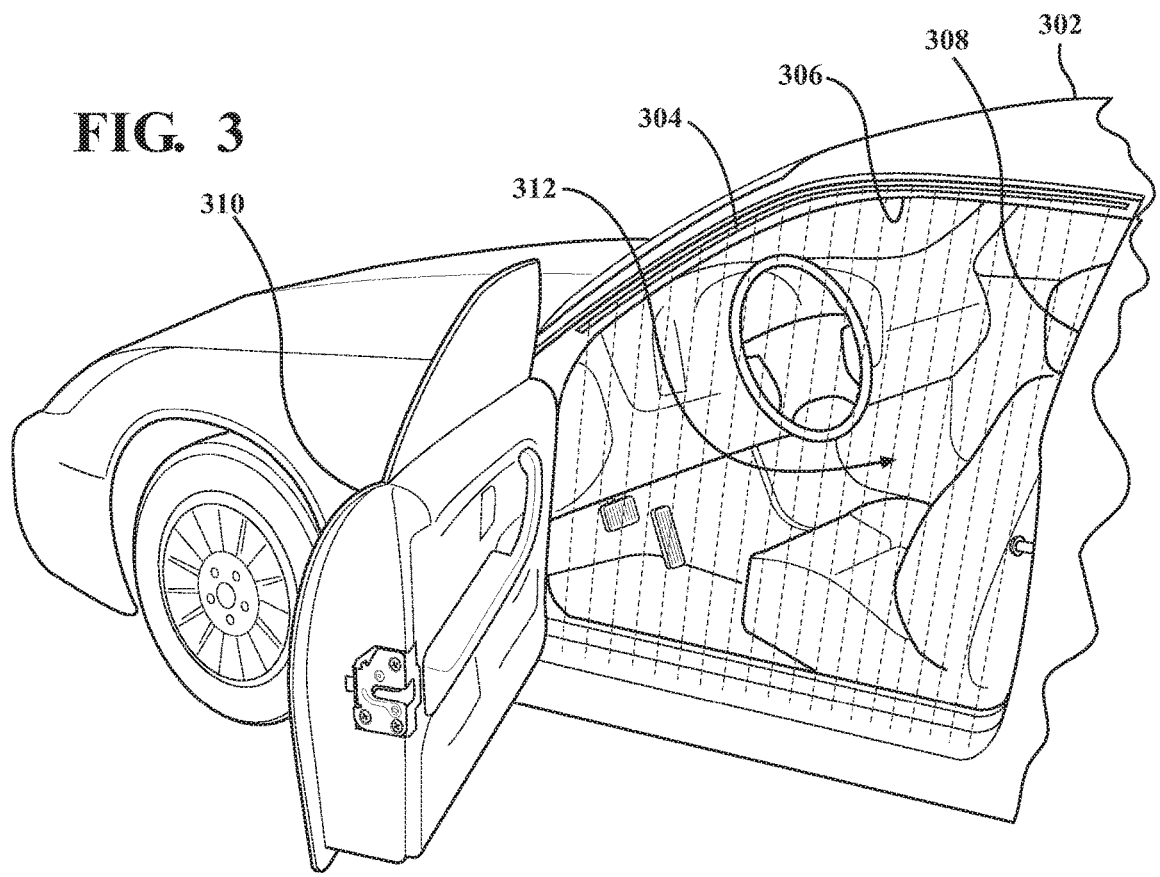
FIG. 3 is an example of a scenario in which one or more ultra-violet sources are operatively positioned with respect to a vehicle door frame.

A non-limiting example of the operation of a vehicle 302, which is similar to the vehicle 102, and/or one or more of the methods will now be described in relation to FIG. 3. FIG. 3 shows an example of a scenario in which one or more ultra-violet sources are operatively positioned with respect to a vehicle door frame. Referring to FIG. 3, the ultra-violet light source(s) 104 can be a plurality of ultra-violet lights 304 operatively connected to a top portion 306 of the vehicle door frame 308 on the driver side of the vehicle 302.

The vehicle 302 can use one or more sensors 120 (such as one or more door position sensors 121) to detect that a vehicle driver door 310 is open, as previously described. The sensor(s) 120 can start a timer 130 upon detecting that the vehicle driver door 310 is open. In response to detecting that the vehicle driver door 310 is open, the ultra-violet light control module(s) 137 can activate the ultra-violet light source(s) 104 such that the ultra-violet light source(s) 104 emits ultra-violet light downwardly across at least a portion of the door frame. A curtain of ultra-violet light can be formed in the door frame. In this way, the outside of the vehicle and the air in the vehicle cabin can be at least partially separated by the ultra-violet light curtain. Thus, the air coming into the vehicle cabin 312 from the outside can be sanitized. Also, any human passenger than passes through the door frame, either entering or exiting the vehicle, can be at least partly sanitized.

Figure 4:
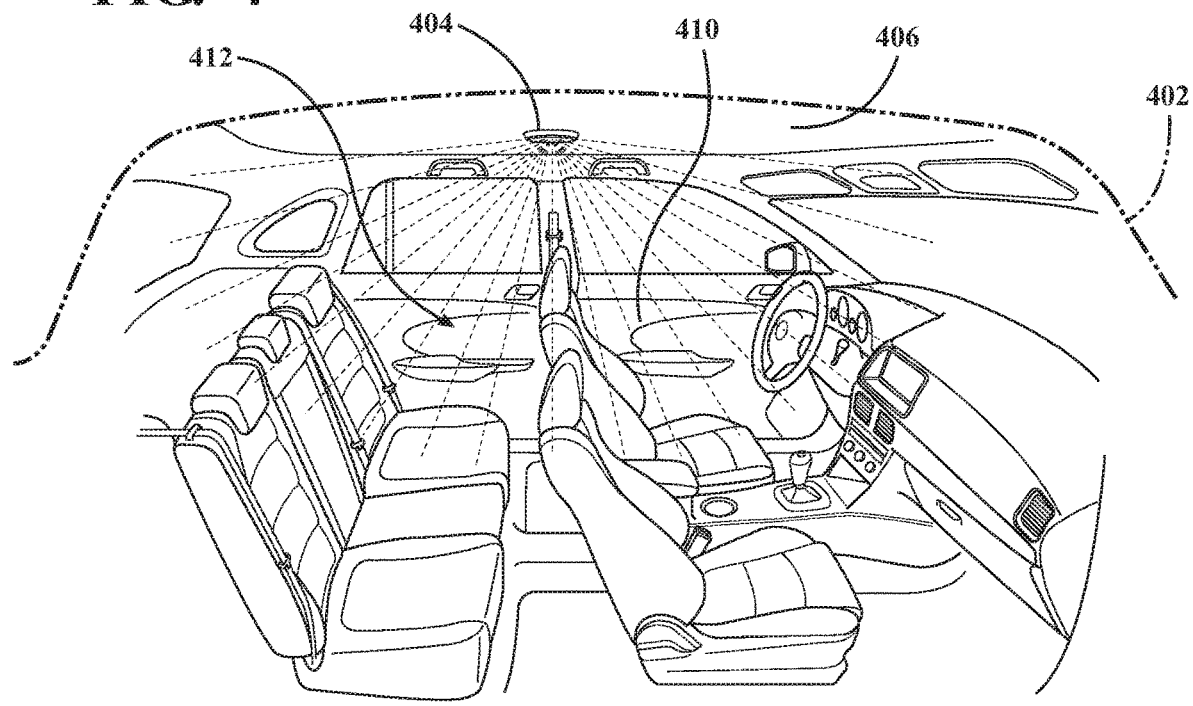
FIG. 4 is an example of a scenario in which the one or more ultra-violet sources are operatively positioned with respect to at least a portion of the vehicle cabin.

Another non-limiting example of the operation of a vehicle 402, which is similar to the vehicle 102, and/or one or more of the methods will now be described in relation to FIG. 4. FIG. 4 shows an example of a scenario in which one or more ultra-violet sources are operatively positioned to emit ultra-violet light in at least a portion of the vehicle cabin. Referring to FIG. 4, the ultra-violet light source(s) 404 can be operatively connected to the ceiling 406 of the vehicle cabin 412 in the vehicle 402.

The vehicle 402 can use one or more sensors 120 (such as one or more door position sensors 121) to detect that the vehicle passenger door 410 is open. In response to detecting that the vehicle passenger door 410 is open, the ultra-violet light control module(s) 137 can cause the ultra-violet light source(s) 404 to be activated such that the ultra-violet light source(s) 404 emits ultra-violet light in the vehicle cabin 412, sanitizing the air in the vehicle cabin 412 and/or the air coming into the vehicle cabin 412. Also, any human occupants or items in the cabin can be at least partly sanitized.

It will be appreciated that arrangements described herein can provide numerous benefits, including one or more of the benefits mentioned herein. For example, arrangements described herein can sanitize a portion of the vehicle. Further, arrangements described herein can reduce the likelihood that contaminated air from outside the vehicle enters the vehicle cabin. Arrangements described herein can sanitize human occupants of the vehicle. Arrangements described herein can sanitize vehicle surfaces and/or items in the vehicle cabin.

The terms "a" and "an," as used herein, are defined as one or more than one. The term "plurality," as used herein, is defined as two or more than two. The term "another," as used herein, is defined as at least a second or more. The terms "including" and/or "having," as used herein, are defined as comprising (i.e. open language). The term "or" is intended to mean an inclusive "or" rather than an exclusive "or." The phrase "at least one of . . . and . . . " as used herein refers to and encompasses any and all possible combinations of one or more of the associated listed items. As an example, the phrase "at least one of A, B and C" includes A only, B only, C only, or any combination thereof (e.g. AB, AC, BC or ABC).

Aspects herein can be embodied in other forms without departing from the spirit or essential attributes thereof. Accordingly, reference should be made to the following claims, rather than to the foregoing specification, as indicating the scope of the invention.

What is claimed is:

1. A system comprising:
a vehicle including a vehicle door;
one or more sensors, the one or more sensors being configured to detect whether the vehicle door is open or closed;
one or more ultra-violet light sources; and
one or more processors, the one or more processors being operatively connected to selectively activate or deactivate the one or more ultra-violet light sources, the one or more processors being programmed to initiate executable operations comprising:
responsive to detecting that the vehicle door is open, cause the one or more ultra-violet light sources to be activated, whereby ultra-violet light is emitted by the one or more ultra-violet light sources with respect to at least a portion of the vehicle.

2. The system of claim 1, wherein the executable operations further include:
responsive to detecting that the vehicle door is closed, cause the one or more ultra-violet light sources to be deactivated or remain deactivated, whereby ultra-violet light is not emitted by the one or more ultra-violet light sources.

3. The system of claim 1, wherein the executable operations further include:
responsive to the vehicle door being open for a predetermined time period, cause the one or more ultra-violet light sources to be deactivated.

4. The system of claim 1, wherein the one or more ultra-violet light sources are operatively positioned with respect to a vehicle door frame.

5. The system of claim 4, wherein the one or more ultra-violet light sources are configured to emit ultra-violet light across the vehicle door frame, whereby the one or more ultra-violet light sources generate an ultra-violet light curtain that at least partially separates a vehicle cabin and an external environment of the vehicle.

6. The system of claim 1, wherein the one or more ultra-violet light sources are operatively positioned to emit ultra-violet light in at least a portion of a vehicle cabin.

7. The system of claim 6, wherein the one or more ultra-violet light sources are operatively connected to a portion of the vehicle cabin.

8. The system of claim 1, wherein the vehicle door is a vehicle driver door.

9. The system of claim 1, wherein the one or more ultra-violet light sources are operatively positioned to emit ultra-violet light downwardly.

10. The system of claim 1, wherein the one or more ultra-violet light sources are configured to emit ultra-violet C (UVC) light.

\* \* \* \* \*